United States Patent
Lee et al.

[11] Patent Number: 4,990,780
[45] Date of Patent: Feb. 5, 1991

[54] METHOD FOR DETERMINING FUEL AND ENGINE OIL COMSUMPTION USING TUNABLE DIODE LASER SPECTROSCOPY

[75] Inventors: Peter S. Lee, Troy; Richard F. Majkowski, Southfield; Richard M. Schreck, Bloomfield Hills, all of Mich.

[73] Assignee: General Motors Corporation, Detroit, Mich.

[21] Appl. No.: 367,906

[22] Filed: Jun. 19, 1989

[51] Int. Cl.$^5$ .......................................... G01N 21/59
[52] U.S. Cl. .................................. 250/343; 250/339; 250/340
[58] Field of Search .................... 250/343, 340, 339

[56] References Cited

PUBLICATIONS

G. J. Kemeny, R. S. Eng and A. W. Mantz, "Utilization of Tunable Infrared Diode Lasers for the Determination of Labelled Molecules in Gas Mixtures", *Acta Physica Academiae Scientarium Hungaricae*, Tomus [Vol.] 48, No. 1 (1980) pp. 93–102.
"The Clinical Spectrum", *Scientific American, Dec. issue, variously identified as 1985 or 1987.*

*Primary Examiner*—Constantine Hannaher
*Attorney, Agent, or Firm*—Domenica N. S. Hartman

[57] ABSTRACT

A method is provided for precisely and concurrently measuring dynamic engine oil consumption and fuel consumption within an internal combustion engine in an automotive environment on a real time basis. Nonradioactive tracer compounds, such as bromine or chlorine in the form of organic bromo- or chloro-compounds are added to the engine oil in small amounts. Upon complete combustion, the bromine or chlorine is converted into either hydrogen bromide or hydrogen chloride. A sample of the exhaust gases generated by the internal combustion engine and comprising the hydrogen bromide or hydrogen chloride is collected and maintained at a pressure where distinction between an absorption line of the tracer specie and the absorption lines of a related isotopic species is discernible. Monochromatic radiation is then transmitted through the gaseous sample at the frequency of an absorption line particular to the tracer specie. Because of the high spectral power density and spectral resolution of the preferred tunable diode lasers, tunable diode laser spectroscopy may be used to measure the amount of tracer isotope within the resultant HCl or HBr gases in the exhaust gases. Corresponding fuel consumption may also be determined from the $CO_2$ in the exhaust gases by similar methods.

2 Claims, 1 Drawing Sheet

METHOD FOR DETERMINING FUEL AND ENGINE OIL COMSUMPTION USING TUNABLE DIODE LASER SPECTROSCOPY

This invention relates to a method for determining fuel and engine oil consumption in an internal combustion engine. More particularly, this invention relates to a method for determining such consumption which utilizes laser spectroscopy of nonradioactive stable isotopes.

BACKGROUND OF THE INVENTION

For evaluating the performance of an internal combustion engine and the corresponding engine design development, it is desirable to provide dynamic measurements of the fuel and engine oil consumption during operation of the internal combustion engine. Currently, the available methods for determining oil consumption are primarily (1) the use of a dipstick, (2) the drain-weigh technique, (3) radiometric techniques and (4) sulfur methods. However, there are serious shortcomings particular to each of these methods. In addition there are shortcomings common to all of these methods such as their failure to provide real time analysis of oil consumption and their failure to provide information on related fuel consumption during the engine operation.

With regards to the traditional dipstick and drain-weigh techniques, many hours of engine operation are required before enough oil is consumed to obtain repeatable and predictable measurements using these rather imprecise methods. As an example, it is assumed that an engine operating at 50 miles per hour will consume oil at the rate of approximately 5,000 miles per quart, therefore, accordingly it will consume approximately 0.01 quarts of oil per hour. Due to the excessive periods of operation required before measurements may be made using these techniques, information on the time resolution of engine operation is prohibited. In addition, these techniques are susceptible to a high degree of inaccuracy, since any losses due to oil seal leaks or retention of the oil in other engine parts will lead to an over estimate of oil consumption, while an underestimate of oil consumption may occur due to fuel dissolution with the oil.

An alternative method for determining consumption is known in the art and is based on the monitoring of sulfur dioxide ($SO_2$), either photometrically or coulometrically, generated from the sulfur in the engine oil during engine operation. This method requires sulfur free isooctane fuel, which therefore undesirably limits the adaptability of this method. In addition, extensive equipment and manpower are required to maintain the test system. Lastly, this method is also subject to interferences from other major or minor exhaust gas components.

The radiometric method is also known and employed by the art. The radiometric method provides a very precise method for measuring oil consumption. This method involves adding the radioactive bromine tracer of 1, 2-dibromooctadecane to the oil. The resultant combustion product from the internal combustion engine is trapped within a sodium hydroxide solution and counted by scintillation counting. This method is undesirable, even though extremely accurate, because of the significant radioactive health and safety considerations and regulatory requirements necessary for its use. In addition, another shortcoming of this method is that it is essentially a batch process which does not readily lend itself to individual measurements, and further requires the preparation of a fresh bromine tracer for each batch operation because of the short half life of the radioactive bromine tracer.

Therefore, there is a definite need in the art for an alternative method for measuring oil consumption during operation of an internal combustion engine in automotive applications. Further, it is desirable that the provided method for determining oil consumption be simple and precise, permit real time measurements and additionally provide concurrent dynamic fuel consumption data.

SUMMARY OF THE INVENTION

It is an object of the present invention to provide a method for concurrently measuring fuel and engine oil consumption in an internal combustion engine.

It is a further object of this invention that such method utilizes a tunable diode laser spectrometer.

Lastly, it is still a further object of this invention that this method provides concurrent, real time, simple and precise measurements of fuel and engine oil consumption, all without undue health and safety considerations.

In accordance with a preferred embodiment of this invention these and other objects and advantages are accomplished as follows.

A method is provided for precisely and concurrently measuring dynamic engine oil consumption and fuel consumption within an internal combustion engine in an automotive environment on a real time basis. This method provides significant input to the testing of engine design parameters and engine performance under realistic operating conditions.

With this method, nonradioactive tracer compounds, such as bromine or chlorine in the form of organic bromo- or chloro- compounds are added to the engine oil in small amounts. Upon complete combustion, the bromine or chlorine is converted into either hydrogen bromide (HBr) or hydrogen chloride (HCl). A sample of the exhaust gases generated by the internal combustion engine and comprising the hydrogen bromide or hydrogen chloride is collected and maintained at a pressure where distinction between an absorption line of the tracer specie and the absorption lines of a related isotopic species is discernible. Monochromatic radiation is then transmitted through the gaseous sample at the frequency of an absorption line for the tracer specie. Because of the high spectral power density and spectral resolution of the preferred tunable diode lasers, tunable diode laser spectroscopy may be used to measure the amount of tracer isotope within the resultant HCl or HBr gases in the exhaust gases. This technique may also be used to determine the corresponding fuel consumption from the $CO_2$ in the exhaust gases.

Other objects and advantages of this invention will be better appreciated from a detailed description thereof which follows.

DETAILED DESCRIPTION OF THE INVENTION

Figure 1:
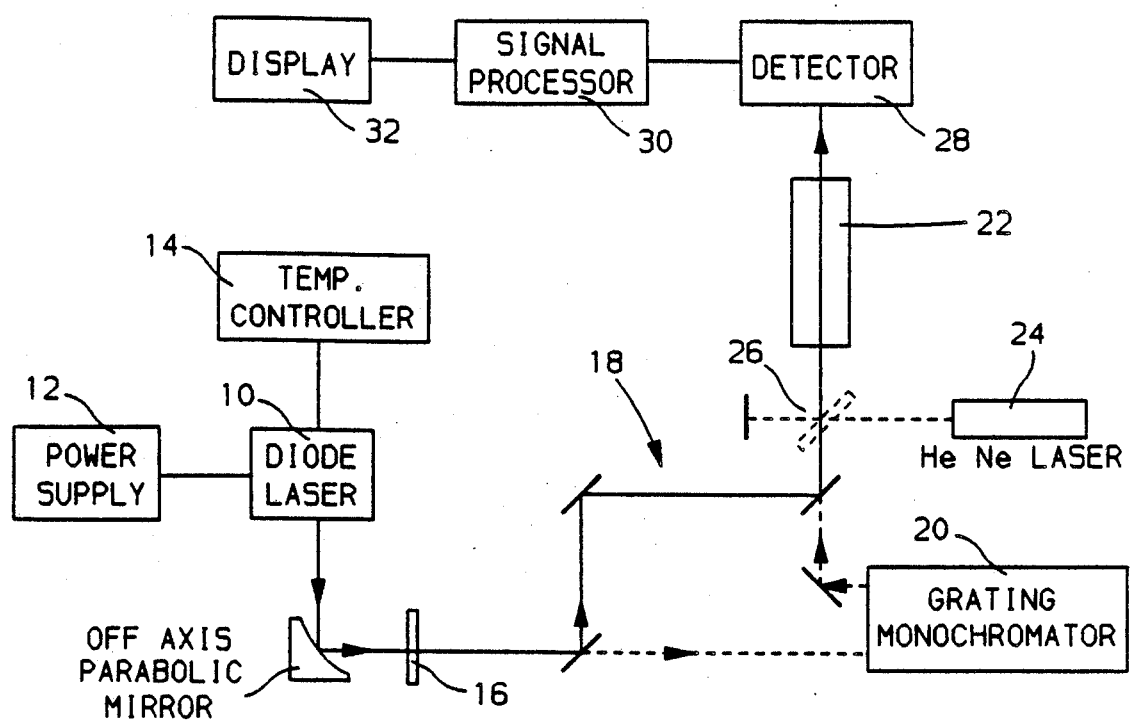
FIG. 1 is a schematic of the tunable diode laser spectrometer system in accordance with a preferred embodiment of this invention.

Nonradioactive stable isotopes of bromine or chlorine are added to the engine oil in small amounts in their natural abundance. The nonradioactive stable isotopes of bromine or chlorine are preferably in the form of organic bromo- or chloro- compounds matched to the volatility of the engine oil. Upon complete combustion, the chlorine or bromine is converted into hydrogen chloride or hydrogen bromide. A tunable diode laser spectrometer is used to determine the amount of tracer isotope in the resultant HCl or HBr of the exhaust gases. The tunable diode laser is characterized by a high spectral power density and spectral resolution better than approximately 0.0001 wave number. In addition, during operation of an automobile, the ratio of fuel-to-oil consumption is generally about 1000:1. Therefore virtually all of the carbon dioxide found in the exhaust comes from the combustion of fuel. Simultaneous detection and measurement of exhaust carbon dioxide accordingly provides useful information on fuel consumption.

The expected concentration of the HCl or HBr in the exhaust gas may be determined from the following assumptions.

Assuming that the fuel economy of an automobile is approximately 20 miles per gallon at a speed of about b 50 miles per hour, and further assuming that about 5,000 miles per quart is the typical oil consumption, then the oil consumption rate is approximately 0.17 milliliters per minute.

In addition, the air-to-fuel mass ratio in a running car is typically about 14.5:1. The exhaust volume may be estimated by this intake air flow. Thus for a car operating at a speed of approximately 50 miles per hour and consuming approximately 20 miles per gallon of fuel the exhaust flow is estimated to be approximately 1,542 liters per minute at standard temperature and pressure, assuming about 750 grams per liter is the density of fuel, and about 1.293 grams per liter is the density of air at standard temperature and pressure.

For the conventional method of radiometric measurement of oil consumption, the total amount of bromine added to the fuel is 0.05 percent. Bromine is in the form of preferably an organobromine compound such as 1, 2-dibromooctadecane. Therefore, for this preferred laser spectroscopy method, if the same amount of this nonradioactive bromine compound is added to the oil, the amount of exhaust hydrogen bromide is estimated to be approximately:

$$\frac{0.17 \text{ ml/min} \times 0.84 \text{ gm/ml} \times 0.05\% \times 22.4 \text{ liter/mole}}{80 \text{ gm/mole}} = 2 \times 10^{-5}$$

liters per minute at standard temperature and pressure, and assuming about 0.84 grams per milliliter is the density of oil, about 0.17 milliliters per minute is the estimated oil consumption rate, and about 80 grams per mole is the atomic weight of bromine. From the above numbers, the concentration of exhaust hydrogen bromide is estimated to be approximately:

$$\frac{2 \times 10^{-5} \text{ liter/min}}{1542 \text{ liter/min}} = \text{about } 13.0 \times 10^{-9}.$$

Therefore, the amount of HBr in the exhaust gases is approximately 13 parts per billion (volume).

For the same amount of chlorine, i.e., approximately 0.05 percent in the oil, in the form of an organochlorine compound such as 1, 2 dichlorooctadecane or organochlorine compound with a carbon number in the range of 18–35, the expected concentration of exhaust hydrogen chloride is estimated to be approximately 29 parts per billion using the analogous calculations and assumptions for the bromine compound. These minute levels are detectable and measurable using our laser spectrometer system due to the high spectral power density and spectral resolution of the laser spectrometer. The measurements may be made even simpler if the amount of organobromine or organochlorine compound which is added to the oil is increased. This is feasible so long as there are no deleterious effects on the operation of the engine.

For bromine tracers, there are two naturally occurring isotopes, $^{79}$Br and $^{81}$Br, with relative abundances of approximately 50.5 percent and approximately 49.5 percent, respectively. The strong infrared transitions of hydrogen bromide are in the frequency range of approximately 2400–2700 cm$^{-1}$, with approximately 10 cm$^{-1}$ to approximately 16 cm$^{-1}$ separation between successive vibration rotation lines and with approximately 0.3 cm$^{-1}$ to approximately 0.4 cm$^{-1}$ separation between the isotopic H$^{79}$Br and H$^{81}$Br transition. In the same spectral region, there are weak carbon dioxide vibration-rotation lines. Therefore, simultaneous monitoring of HBr and $CO_2$ would enable the dynamic measurement of both fuel and oil economy at the same time.

The concentration of $CO_2$ in the exhaust gases is typically a few percent, which is about $10^6$ times higher than the concentration of HBr in the exhaust gases. Using conventional techniques, the measurement of a low concentration species may be complicated by the presence of a high concentration species. However, this difficulty is diminished using our technique due to the inverse difference in line intensities of the various gases. There are several spectral regions with adequate line spacings between the HBr and $CO_2$ to effect distinction between the gases and with comparable line intensity values for ease of measurement. In addition, there are some spectral regions where it is feasible to measure both isotopic forms of HBr so as to provide a built-in check on the precision of this preferred laser spectrometer oil consumption measurement.

For chlorine tracers, there are two naturally occurring isotopes, $^{35}$Cl and $^{37}$Cl with naturally occurring abundances of approximately 75.5 percent and approximately 24.5 percent, respectively. The strong vibration-rotation lines are in the frequency range of approximately 2600 cm$^{-1}$ to 3100 cm$^{-1}$ where an approximately 20 cm$^{-1}$ wavelength separation between successive vibration-rotation lines occurs and where approximately 2 cm$^{-1}$ wavelength separation occurs between the comparable vibration-rotation lines of the two isotopic molecules. It is presumed that there are spectral regions where both hydrogen chloride and carbon dioxide gas may be simultaneously measured, such as at 2652 or 2775 cm$^{-1}$, so as to permit concurrent dynamic measurements of oil and fuel consumption. It is also foreseeable that there are spectral regions where hydrogen chloride, hydrogen bromide and carbon dioxide, HCl, HBr and $CO_2$ respectively, may all be measured at the same time.

Tunable diode laser absorption spectroscopy has been used to measure these various components in automotive engine exhaust gas. This preferred spectroscopic system is characterized by the following features. First, all of the optics used are preferably reflective, off-axis parabolic mirrors. This is desirable since reflective optics minimize optical interferences. Second, it is preferred that the first laser beam collection-collimating parabolic mirror be disposed within the diode laser dewar to further reduce the possibilities of interference type optical noises. Third, a heated long path multi-pass all reflection absorption cell, or white cell, is preferably utilized to achieve the high sensitivity required for this extremely minute gas component analysis. The cell is preferably heated to approximately 100° C. Lastly, where windows are needed in the system, either for the tunable diode laser or the detectors or absorption cell, tilted window holders are preferred so that the unwanted reflections are steered out of the optical system.

A typical apparatus for carrying out this preferred method is shown in FIG. 1. The apparatus includes a tunable diode laser 10, a power supply 12 for the laser 10, and a temperature controller 14. The laser is preferably of the IV-VI compounds such as the lead salt type described in the U.S. Pat. Nos. 4,350,990 and 4,186,355 to Lo and 4,577,322 and 4,608,694 to Partin, but may also be of the III-V compounds such as the GaAs types. Such lasers are tuned by varying the operating temperature and are available for operation in the wavelength range of 2.5 to 30 microns for the lead salt type lasers. The laser may be scanned over a small band, about 0.5 to 3 cm$^{-1}$, at a ramping rate of about 500 cycles per second. The laser 10 may also be tuned to emit at a preset wavelength without scanning action to specifically target an absorption peak, for example. Alternatively, scanning or sweeping action allows the entire absorption curve related to a single line to be measured in detail. By varying the injection current, operating parameters of the laser system can be adjusted for a variety of isotopes and molecules. Any infrared active molecule with a suitable spectrum can be studied by this system. The system therefore would be versatile rather than dedicated to a single isotopic species. The isotopic spectral lines are well resolved, thus eliminating any background interference like that encountered in more conventional techniques.

The GaAs types of lasers mentioned above are in a class of shorter wavelength diode lasers composed of III-V compounds involving some of the following elements: Al, Ga, In, P, As and Sb. These lasers may not emit at the fundamental vibration-rotation frequencies but are utilized for combination or overtone bands along with the more sensitive detecting schemes for stable isotope analysis. These shorter wavelength lasers operate at relatively high heat sink temperatures and with shorter wavelength infrared detectors, thereby facilitating the use of inexpensive coolers such as thermoelectric coolers, or require no cooling below room temperature. Laser radiation passes through a chopper 16 and simultaneously through a transfer optics system 18 and grating monochromator 20 to a cell 22 containing the sample gas. The laser 10 is tuned so that this mode spans the absorption line of the desired isotopic molecule. A He-Ne laser 24, a pellicle beam splitter and a plane reflecting mirror 26 mounted on a kinematic base may be used to facilitate the alignment of infrared radiation. During the initial setup, a grating monochromator may be used to provide wavelength identification and to filter out unwanted laser modes. Once the proper conditions for wavelength interval and single mode operation are established, the monochromator can be bypassed. A detector 28 senses the radiation which passes the cell 22 and a signal processor 30 processes the detector signals and provides an output on display 32. In addition the signal processor 30 may be equipped to analyze the signal in accordance with second harmonic detection techniques.

For this preferred method, the measurement is made on a single absorption line in the spectra of the tracer isotopic specie. Such an absorption line is selected from a region free from interference, or alternatively appropriately spaced from the other isotopic species. The sample essentially requires no preparation. In addition, the sample only needs to be maintained at a low enough pressure to eliminate pressure broadening of the spectral lines, e.g., the sample is introduced to the sample cell 22 at an exemplary low pressure of about 25 l torr.

Radiation at the frequency of an absorption line of the isotopic tracer specie of interest is transmitted through the cell 22 and its intensity, I, is measured after passing through the cell 22. To determine the absolute concentration value a measure of the incident radiation intensity, $I_o$, is needed. That value is obtained by evacuating the cell 22 and measuring the intensity of the transmitted radiation at the same frequency after passing through the evacuated cell 22. An alternative method for obtaining the incident radiation intensity, $I_o$, is by tuning the frequency of the radiation to a value, $f_o$, just off the absorption line, that is, near the absorption line but not subject to absorption by that line. The concentration of the tracer specie is determined from the Beer-Lambert law: $I = I_o e^{-apl}$ where p is the pressure of the isotopic molecule (torr), l is the path length (cm) and a is the spectral absorption coefficient of the isotopic molecule. This spectroscopic measurement technique is useful for large isotopic specie concentration.

For low isotopic specie concentration, it is preferable to use wavelength modulation and harmonic detection technique which provides superior signal to noise ratio compared to conventional straight absorption measurement. As the diode laser is slowly tuned over the spectral feature of interest, the wavelength of measurement is modulated at high frequency and with a window small compared to the width of the spectral band. The detector output is processed by a frequency and phase selective amplification system (such as a lock-in amplifier) which is referenced to the modulation frequency. When the detection system is tuned to the second harmonic of the modulation frequency, the output is proportional to the second derivative of the spectral signal. The wavelength modulation is, in effect, averaging the spectral signal a number of times over a small window for each data point. It is important to note that the method is insensitive to any DC component of the signal such as the broad luminescence background emission that may be present in the laser. The spectral peak is related to the concentration of the measured specie by a working curve obtained by calibration of the spectrometer using samples of known concentration. This technique is exceptionally good for measurement of very low concentrations, but a simpler more direct technique, described above, may be used where larger concentrations are to be measured.

Figure 2:
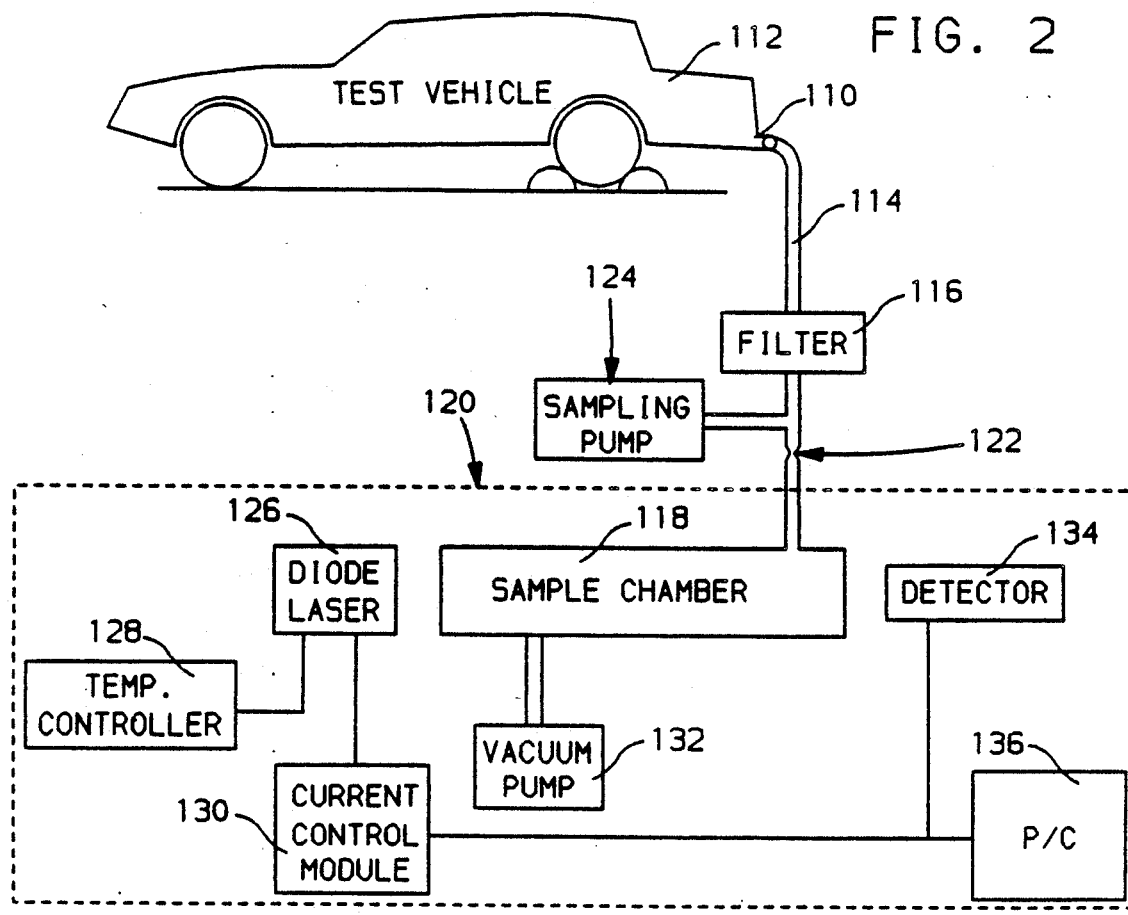
FIG. 2 is a schematic of a tunable diode laser spectrometer arranged to measure exhaust gases from an automotive chassis dynamometer test.

A preferred example of this spectrometer system for automotive exhaust analysis is now described and illustrated in FIG. 2. The measurement of exhaust gas compositions from stationary vehicle tests, such as those conducted on a chassis dynamometer are accomplished with a heated sampling train. Undiluted exhaust gas is drawn from the tailpipe 110 of the test vehicle 112 via a sampling line 114 heated to over approximately 100° C. to prevent condensation of water in the system. The exhaust is preferably absolute filtered 116 to remove particulate matter and a portion of the exhaust is then introduced into the sample chamber 118 of the spectrometer 120 via a calibrated micro-orifice 122 and sampling pump 124. The chamber 118 is maintained at low pressure conditions using a vacuum pump 132. Monochromatic light at the desired wavelength is transmitted through the chamber 118 by means of a preferred tunable diode laser 126, which is maintained at a set temperature by a temperature controller 128 and electrically connected to a current control module 130. A detector 134 analyzes the spectroscopic signals and furnishes the measurements to a computer 136 for further analysis.

The exact dimensions of the sample volume will depend on which isotopic forms of the hydrogen bromide or hydrogen chloride are being used as the tracer for detection of oil consumption. However, in either alternative, after the operating conditions are determined, the chamber 118 volume is minimized and inlet and exit ports are provided to promote rapid throughput of gas for best time resolution of the signal. The actual time resolution is measured by determining instrument response to a bolus of test gas introduced at the entry port and the system dimensions adjusted to maximize performance.

It is anticipated that this configuration is able to simultaneously monitor fuel consumption and oil consumption during conventional multi-mode emission tests and other dynamometer tests of engines or whole vehicles. Measurements of this type taken over very short periods of time, i.e., seconds or minutes, allow comparisons to be made of the effects of component-design modifications on fuel and oil consumption over a wide range of engine operating conditions. This type of testing is currently not possible due to the inaccuracy and long run time necessary to make a measurement with drain and weigh or dipstick techniques. In addition, this system permits the use of a nonradioactive tracer in the fuel and/or oil.

While our invention has been described in terms of a preferred embodiment, it is apparent that other forms could be adopted by one skilled in the art, such as by the use of different laser materials, cooling techniques or the use of fiber optics.

Accordingly the scope of our invention is to be limited only by the following claims.

The embodiments of the invention in which an exclusive property or privilege is claimed are defined as follows:

1. A method for evaluating fuel and engine oil consumption on a near real-time basis in an internal combustion engine comprising the steps of:
   treating the fuel or engine oil with a substance with a nonradioactive organobromine tracer isotope either in its natural abundance or enriched;
   continuously collecting combusted gaseous samples comprising hydrogen bromide from the exhaust gases generated by the internal combustion engine;
   maintaining each of said combusted gaseous sample at a pressure where distinction between an absorption line of said tracer isotopic specie and the absorption lines of related isotopic species is discernible,
   transmitting monochromatic radiation through each of said gaseous samples at the frequency of an absorption line for said tracer isotopic specie,
   while concurrently detecting the intensity of a spectral line for said tracer isotopic specie in each of the samples so as to determine fuel and engine oil consumption in the internal combustion engine on a near real-time basis.

2. A method for evaluating fuel and engine oil consumption on a near real-time basis in an internal combustion engine comprising the steps of:
   treating the fuel or engine oil with a substance enriched with a nonradioactive organochlorine tracer isotope;
   continuously collecting combusted gaseous samples comprising hydrogen chloride from the exhaust gases generated by the internal combustion engine;
   maintaining each of said combusted gaseous sample at a pressure where distinction between an absorption line of said tracer isotopic specie and the absorption lines of related isotopic species is discernible,
   transmitting monochromatic radiation through each of said gaseous samples at the frequency of an absorption line for said tracer isotopic specie,
   while concurrently detecting the intensity of a spectral line for said tracer isotopic specie in each of the samples so as to determine fuel and engine oil consumption in the internal combustion engine on a near real-time basis.

* * * * *